US011752074B2

(12) United States Patent
Lee et al.

(10) Patent No.: US 11,752,074 B2
(45) Date of Patent: Sep. 12, 2023

(54) WARMING CONDITIONER

(71) Applicant: The Procter & Gamble Company, Cincinnati, OH (US)

(72) Inventors: Martin Chang Shou Lee, Singapore (SG); Jun Ji Zhang, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/510,478

(22) Filed: Oct. 26, 2021

(65) Prior Publication Data

US 2022/0125693 A1  Apr. 28, 2022

Related U.S. Application Data

(60) Provisional application No. 63/106,261, filed on Oct. 27, 2020.

(51) Int. Cl.
*A61Q 5/12* (2006.01)
*A61K 8/23* (2006.01)
*A61K 8/41* (2006.01)

(52) U.S. Cl.
CPC ............... *A61K 8/23* (2013.01); *A61K 8/416* (2013.01); *A61Q 5/12* (2013.01); *A61K 2800/242* (2013.01); *A61K 2800/882* (2013.01)

(58) Field of Classification Search
None
See application file for complete search history.

(56) References Cited

U.S. PATENT DOCUMENTS

| | | |
|---|---|---|
| D113,443 S | 2/1939 | Stein |
| D144,732 S | 5/1946 | Radow |
| D198,593 S | 7/1964 | Johns |
| D201,928 S | 8/1965 | Theodore |
| D204,711 S | 5/1966 | Plummer |
| 3,306,500 A | 2/1967 | Williams |
| D216,459 S | 1/1970 | Viitanen |
| D223,995 S | 6/1972 | Beaver |
| 3,702,302 A | 11/1972 | Wilson |
| 3,866,800 A | 2/1975 | Schmitt |
| D239,698 S | 4/1976 | Utley |
| D248,926 S | 8/1978 | Furlong et al. |
| D254,710 S | 4/1980 | Leger |
| D254,954 S | 5/1980 | Ribeiro |
| D275,736 S | 10/1984 | Aldrich |
| D289,855 S | 5/1987 | Carlson |
| D312,780 S | 12/1990 | Demarest |
| 4,984,712 A | 1/1991 | Jouillat |
| D318,620 S | 7/1991 | Kipperman et al. |
| D346,964 S | 5/1994 | Green |
| D348,829 S | 7/1994 | Hallas |
| D351,785 S | 10/1994 | Newell |
| D365,752 S | 1/1996 | Bucher et al. |
| 5,538,720 A | 7/1996 | Jendryssek-pfaff |
| D373,552 S | 9/1996 | Lownsbury |
| D375,051 S | 10/1996 | Gonda et al. |
| D376,762 S | 12/1996 | Fenton et al. |
| D382,808 S | 8/1997 | Fenton |
| D398,238 S | 9/1998 | Bertolini et al. |
| D401,138 S | 11/1998 | Rosen et al. |
| D401,158 S | 11/1998 | Bakic |
| D419,883 S | 2/2000 | Heydenburg et al. |
| D421,391 S | 3/2000 | Anderson et al. |
| D427,073 S | 6/2000 | Gaffney et al. |
| 6,082,588 A | 7/2000 | Markey |
| D428,816 S | 8/2000 | Ito et al. |
| D430,802 S | 9/2000 | Adachi et al. |
| 6,129,243 A | 10/2000 | Pal et al. |
| D435,098 S | 12/2000 | Kemmis et al. |
| D446,725 S | 8/2001 | Lloyd |
| 6,274,128 B1 | 8/2001 | Bergmann |
| D447,954 S | 9/2001 | Cummings |
| D451,402 S | 12/2001 | Kokenge et al. |
| D458,847 S | 6/2002 | Kuzma et al. |
| D463,744 S | 10/2002 | Brozell |
| D464,266 S | 10/2002 | Dalmau |

(Continued)

FOREIGN PATENT DOCUMENTS

| | | |
|---|---|---|
| CN | 101039721 A | 9/2007 |
| CN | 101198311 A | 6/2008 |

(Continued)

OTHER PUBLICATIONS

Astrqle 24PCS Clear Refillable Empty Plastic Squeeze Soft Tubes. Date first available: Oct. 13, 2017. Site visited: Sep. 2, 2022. Available online: a target="_blank" href="https://www.amazon.com/Refillable-Plastic-Squeeze-Container-Cleanser/dp/BO76F2QGSG"https://www.amazon.com/Refillable-Plastic-Squeeze-Container-Cleanser/dp/BO76F2QGSG/a (Year: 2017).

LageenTubes post on LageenTubes LTD Facebook Page. Date posted on Facebook: Sep. 7, 2020. Site visited: Aug. 25, 2022. brAvailable online: a target="_blank" href="https://www.facebook.com/lageentubes/posts/pfbidOMqrYDX300MPHVJGvGzUQvpWAJT1J4tfU5A8LqCm2FOS1Rxj38bl1ZXLyqS7kHGVnl"https://www.facebook.com/lageentubes/posts/pfbidOMqrYDX300MPHVJGvGzUQvpWAJT1J4tfU5A8LqCm2FOS1Rxj38bl1ZXLyqS7kHGVnl/a (Year: 2020).

(Continued)

*Primary Examiner* — Jyothsna A Venkat
(74) *Attorney, Agent, or Firm* — Kathleen Y. Carter (57) ABSTRACT

A cosmetic composition comprising a first composition comprising an inorganic heat generating agent that generates a heat by mixing with water; and a second composition comprising a cationic surfactant system comprising a monoalkyl quaternized ammonium salt cationic surfactant, a high melting point fatty compound, and an aqueous carrier; wherein the ratio of the first composition to the second composition is from about 35:65 to 98:2; the difference in viscosities between the first and second composition is less than 3.5 Pa·s; the first and second compositions are kept separate from one another until dispensed; and the cosmetic composition when dispensed has a warming benefit.

4 Claims, 2 Drawing Sheets

(56) References Cited

U.S. PATENT DOCUMENTS

| | | |
|---|---|---|
| D470,055 S | 2/2003 | Blair et al. |
| D480,955 S | 10/2003 | Perlowski et al. |
| D481,950 S | 11/2003 | Bakic |
| D485,764 S | 1/2004 | Bakic |
| D492,603 S | 7/2004 | Rashid |
| D494,870 S | 8/2004 | Bakic |
| 6,877,638 B2 | 4/2005 | Chan |
| D508,407 S | 8/2005 | Busch et al. |
| D510,135 S | 9/2005 | Mariotti |
| D522,876 S | 6/2006 | Braaten et al. |
| D526,568 S | 8/2006 | Bakic |
| D530,618 S | 10/2006 | Estabrook et al. |
| D531,906 S | 11/2006 | Mongeon et al. |
| D533,066 S | 12/2006 | Mongeon et al. |
| D547,671 S | 7/2007 | Penfold et al. |
| D551,088 S | 9/2007 | Dittmer et al. |
| D553,254 S | 10/2007 | Colin et al. |
| D578,892 S | 10/2008 | Bridgman et al. |
| D583,254 S | 12/2008 | Odonahue |
| D586,218 S | 2/2009 | Mongeon et al. |
| D586,220 S | 2/2009 | Bridgman et al. |
| D588,459 S | 3/2009 | Davis et al. |
| D590,259 S | 4/2009 | Kunesh et al. |
| D601,035 S | 9/2009 | Rangaswamy et al. |
| D614,031 S | 4/2010 | Creed et al. |
| D614,494 S | 4/2010 | Palmer et al. |
| D624,424 S | 9/2010 | Fiore et al. |
| D625,604 S | 10/2010 | Zaslow |
| D640,929 S | 7/2011 | Swanson |
| D642,061 S | 7/2011 | Bowers et al. |
| 8,052,016 B2 | 11/2011 | Wang |
| D656,832 S | 4/2012 | Bowers et al. |
| 8,413,845 B1 | 4/2013 | Duncan |
| D683,631 S | 6/2013 | Crawford |
| D686,666 S | 7/2013 | Lee et al. |
| D709,381 S | 7/2014 | Mochizuki et al. |
| D710,708 S | 8/2014 | Gebhardt |
| D715,149 S | 10/2014 | Brewer et al. |
| D746,692 S | 1/2016 | Alvarez et al. |
| D749,955 S | 2/2016 | Staten et al. |
| D751,904 S | 3/2016 | Landrum et al. |
| D751,911 S | 3/2016 | Alvarez et al. |
| D753,505 S | 4/2016 | Landrum et al. |
| D775,966 S | 1/2017 | Jeong |
| D777,039 S | 1/2017 | Sahatjian |
| D780,594 S | 3/2017 | Harris et al. |
| D804,320 S | 12/2017 | Harris et al. |
| D807,195 S | 1/2018 | Richmond |
| D813,031 S | 3/2018 | Boston et al. |
| D813,679 S | 3/2018 | Bos et al. |
| D813,687 S | 3/2018 | Ferreira et al. |
| D821,878 S | 7/2018 | Cannamela et al. |
| D827,444 S | 9/2018 | Oates |
| D844,448 S | 4/2019 | Miller et al. |
| D845,315 S | 4/2019 | Malahy et al. |
| 10,335,818 B2 | 7/2019 | Pointel |
| D863,966 S | 10/2019 | Kauffman et al. |
| D879,615 S | 3/2020 | Young |
| D891,935 S | 8/2020 | Lee et al. |
| D895,432 S | 9/2020 | Yoshioka |
| D897,213 S | 9/2020 | Eyal |
| D898,578 S | 10/2020 | McGreevy |
| D900,617 S | 11/2020 | Repellin |
| D915,123 S | 4/2021 | Dos Santos Sabino Serra |
| D920,802 S | 6/2021 | Davis |
| D920,803 S | 6/2021 | Davis |
| D925,365 S | 7/2021 | Conceicao et al. |
| D925,366 S | 7/2021 | Conceicao et al. |
| D925,374 S | 7/2021 | Escobar |
| D926,582 S | 8/2021 | Sahatjian |
| D932,912 S | 10/2021 | Cox et al. |
| D932,915 S | 10/2021 | Cox et al. |
| D953,170 S | 5/2022 | Marotti et al. |
| D955,221 S | 6/2022 | Miller et al. |
| D971,735 S | 12/2022 | Van Den Bergh et al. |
| D974,181 S | 1/2023 | Ovitt et al. |
| 2004/0028711 A1 | 2/2004 | Uchida |
| 2005/0189314 A1 | 9/2005 | Carbone |
| 2006/0078528 A1 | 4/2006 | Yang et al. |
| 2007/0041929 A1 | 2/2007 | Torgerson |
| 2007/0095702 A1 | 5/2007 | Park et al. |
| 2007/0119861 A1 | 5/2007 | Bhagwat |
| 2007/0136937 A1 | 6/2007 | Sawalski et al. |
| 2007/0196403 A1 | 8/2007 | Uchida et al. |
| 2008/0128423 A1 | 6/2008 | Rick |
| 2008/0128425 A1 | 6/2008 | Rick et al. |
| 2008/0128426 A1 | 6/2008 | Rick |
| 2009/0152294 A1 | 6/2009 | Mizell |
| 2011/0259914 A1 | 10/2011 | Lee |
| 2014/0230842 A1 | 8/2014 | Parris |
| 2014/0263448 A1 | 9/2014 | Erskine-smith |
| 2014/0290685 A1 | 10/2014 | Battermann |
| 2014/0335040 A1 | 11/2014 | Yu et al. |
| 2015/0093347 A1 | 4/2015 | Uehara et al. |
| 2015/0157544 A1 | 6/2015 | Briggs et al. |
| 2015/0208859 A1 | 7/2015 | Wang |
| 2015/0216786 A1 | 8/2015 | Yu et al. |
| 2016/0374919 A1 | 12/2016 | Hakozaki |
| 2017/0246093 A1 | 8/2017 | Horne |
| 2018/0360725 A1 | 12/2018 | Hoffmann et al. |
| 2020/0000689 A1 | 1/2020 | Zukowski |
| 2020/0093731 A1 | 3/2020 | Brac De La Perriere et al. |
| 2021/0008578 A1 | 1/2021 | Bartolucci et al. |
| 2021/0009336 A1 | 1/2021 | Bartolucci et al. |
| 2021/0059925 A1 | 3/2021 | Lee et al. |
| 2021/0059926 A1 | 3/2021 | Lee et al. |
| 2021/0069081 A1 | 3/2021 | Hiruma et al. |
| 2021/0128422 A1 | 5/2021 | Zukowski et al. |
| 2021/0128436 A1 | 5/2021 | Zukowski et al. |
| 2021/0137244 A1 | 5/2021 | Zukowski et al. |
| 2021/0206141 A1 | 7/2021 | Neufarth et al. |

FOREIGN PATENT DOCUMENTS

| | | |
|---|---|---|
| CN | 103561712 A | 2/2014 |
| CN | 104918661 A | 9/2015 |
| CN | 105899183 A | 8/2016 |
| CN | 304430622 | 12/2017 |
| CN | 304655558 | 6/2018 |
| CN | 306147636 | 11/2020 |
| CN | 306147639 | 11/2020 |
| CN | 306180534 | 11/2020 |
| CN | 306743842 S | 10/2021 |
| CN | 370300046 | 4/2022 |
| DE | 3141746 A1 | 5/1983 |
| DE | 19806786 A1 | 8/1999 |
| EP | 0586929 A1 | 3/1994 |
| EP | 1516613 A1 | 3/2005 |
| EP | 1787634 A1 | 5/2007 |
| GB | 6106424 | 11/2020 |
| JP | H0680534 A | 3/1994 |
| JP | H06100411 A | 4/1994 |
| JP | H1160460 A | 3/1999 |
| JP | 2008074779 A | 4/2008 |
| JP | 2013040153 A | 2/2013 |
| JP | 2013103920 A | 5/2013 |
| JP | 2016507592 A | 3/2016 |
| JP | 2017210413 A | 11/2017 |
| JP | 2017210472 A | 11/2017 |
| JP | 2019123710 A | 7/2019 |
| KR | 20040062500 A | 7/2004 |
| KR | 20080107654 A | 12/2008 |
| KR | 20110113892 A | 10/2011 |
| KR | 20120079508 A | 7/2012 |
| KR | 20200122083 A | 10/2020 |
| WO | 0219977 A1 | 3/2002 |
| WO | 2004035016 A1 | 4/2004 |
| WO | 2014124066 A1 | 8/2014 |
| WO | 2015024078 A1 | 2/2015 |
| WO | 2017057784 A1 | 4/2017 |
| WO | 2017115827 A1 | 7/2017 |
| WO | 2017116552 A1 | 7/2017 |

(56) References Cited

FOREIGN PATENT DOCUMENTS

OTHER PUBLICATIONS

Rejoice Shampoo Anti Dandruff 3 in 1600ml—Gives You Smooth Hair and has Anti-Dandruff ZPT which Helps Prevent The Recurrence of Dandruff in Your Hair. Online, published date Feb. 28, 2019. Retrieved on Jun. 8, 2022 from URL: https://www.amazon.com/Rejoice-Shampoo-Dandruff-Anti-Dandruff-Recurrence/dp/B07NK7488G/ref=sr_.

Revlonissimo Colorsmetiqueta Permanent Hair Color Mixers. Date first available: 2022. Site visited: Aug. 25, 2022. Available online: a href="https://www.revlonprofessional.com/product/revlonissimo-colorsmetique-permanent-hair-color-mixers/" target="_blank"https://www.revlonprofessional.com/product/revlonissimo-colorsmetique-permanent-hair-color-mixers//a (Year: 2022).

Set of 3—White and Grey Refillable Reusable Personalised Pump Dispenser Bottles for Shampoo & Conditioner. Mrs HinchInspired. Eco Friendly. Christmas Present for Mum. Christmas Present for Women. Online, published date Jul. 5, 2019. Retrieved on Jun. 26, 2022 from URL: https://www.amazon.co.uk/Refillable-Personalise.

All Office Actions; U.S. Appl. No. 17/893,262, filed Aug. 23, 2022.

U.S. Unpublished Patent Application U.S. Appl. No. 17/893,262, filed Aug. 23, 2022, to Michele Tsu Fern Chua et al.

All Office Actions; U.S. Appl. No. 17/005,411, filed Aug. 28, 2020.

All Office Actions; U.S. Appl. No. 17/005,416, filed Aug. 28, 2020.

Database GNPD [Online], Mintel, Anonymous, "Cleansing Oil Creme Duo", XP055758338, Database accession No. 4686899, dated May 9, 2017, pp. 1-3.

15802 PCT Search Report and Written Opinion for PCT/US2021/072037 dated Mar. 7, 2022, 16 pages.

Database GNPD [Online] Mintel: anonymous: "Heat Mask", dated Apr. 25, 2017 (Apr. 25, 2017), pp. 3, XP055894037, Database accession No. 4760985.

Database GNPD [Online] Mintel; anonymous: "Warming Express Mask", dated Jul. 10, 2018 (Jul. 10, 2018), pp. 3, XP055894031, Database accession No. 5825017.

WARMING CONDITIONER

FIELD OF THE INVENTION

The present invention relates to a dual-phase cosmetic composition that upon dispensing provides warming and hair conditioning.

BACKGROUND OF THE INVENTION

A variety of hair conditioning products are available to consumers. In general, hair conditioners are used to improve the feel, appearance, and manageability of hair. While some conditioners optimize the performance and results of the conditioner on hair, other conditioners focus on the consumer experience. For example, some conditioners may include components that generate heat and provide a pleasant user experience. There exists a continuing need for hair conditioners that combine a pleasant, warming consumer experience with high performance conditioning results.

SUMMARY OF THE INVENTION

A cosmetic composition comprising:
(a) a first composition comprising an inorganic heat generating agent that generates a heat by mixing with water; and
(b) a second composition comprising cationic surfactant system comprising a mono-alkyl quaternized ammonium salt cationic surfactant; a high melting point fatty compound, and an aqueous carrier;
wherein the ratio of the first composition to the second composition is from about 35:65 to 98:2;
wherein the difference in viscosities between the first and second composition is less than 3.5 Pa·s;
wherein the first and second compositions are kept separate from one another until dispensed;
and wherein the cosmetic composition when dispensed has a warming benefit.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated. The weight average molecular weight may be measured by gel permeation chromatography.

"QS" means sufficient quantity for 100%.

DETAILED DESCRIPTION

The cosmetic composition of the present invention may comprise a first composition and a second composition, wherein the first and second compositions are kept separate from one another until dispensed. The first composition comprises an inorganic heat generating agent and the second composition comprises a cationic surfactant system comprising a mono-alkyl quaternized ammonium salt cationic surfactant, a high melting point fatty compound, and an aqueous carrier. Although kept separate until dispensing, the first composition and the second composition are put into contact upon dispensing.

Consumers expect certain performance and benefits from their hair conditioner. For example, they desire the conditioner's appearance to be thick, rich, and homogeneous, along with suitable rheology. Consumers additionally want a superb performance from their conditioner, such as a moisturized feel, softness, and static control after use. Such performance benefits may be provided through the use of a cationic surfactant system and a high melting point fatty compound combined in an aqueous carrier. Some conditioners also provide heating when used. Such heating may be triggered by water in the shower or bath as the consumer uses the conditioner. Because the heating is provided by certain components of the conditioner mixing with water, a heating conditioner typically is not an aqueous formulation. Thus, there can be a trade-off between providing the heating experience during use to consumers and providing the optimal performance benefits to consumers all in a single hair conditioning product. The present invention uses a multi-phase product that is able to provide the best of both worlds.

First Composition

In one phase of the present invention is a first composition that comprises an inorganic heat generating agent that generates heat by mixing with water. As the heating reaction does not begin until mixed with water, the carrier of the first composition is anhydrous.

As used in the present invention, "anhydrous" means that the compositions contain 5% or less of water. The anhydrous compositions of the first composition contain, preferably 3% or less, more preferably 1% or less, still more preferably substantially free of water. The anhydrous compositions warm to a temperature of, preferably from about 25° C. to about 80° C., more preferably from about 30° C. to about 60° C., still more preferably from about 35° C. to about 45° C. This temperature can be adjusted by, for example, choosing the heat generating agents, the amount of the heat generating agent, and additional agents which can control the heat generating reaction.

The inorganic heat generating agents that may be used, such as calcium sulfate, generally have an enthalpy change of about −19.2 kJ mol$^{-1}$ and below. The inorganic heat generating agents useful herein may include, for example, chlorides, such as calcium chloride ($CaCl_2$, $CaCl_2 \cdot H_2O$, $CaCl_2 \cdot 2H_2O$), magnesium chloride ($MgCl_2$, $MgCl_2 \cdot 2H_2O$, $MgCl_2 \cdot 4H_2O$), aluminum chloride ($AlCl_3$, $AlCl_3 \cdot 6H_2O$), ferric chloride ($FeCl_3$, $FeCl_3 \cdot 2H_2O$), and zinc chloride ($ZnCl_2$); sulfates such as magnesium sulfate ($MgSO_4$, $MgSO_4 \cdot H_2O$, $MgSO_4 \cdot 4H_2O$), zinc sulfate ($ZnSO_4 \cdot H_2O$), ferrous sulfate ($FeSO_4$, $FeSO_4 \cdot H_2O$), and calcium sulfate ($CaSO_4$, $CaSO_4 \cdot \frac{1}{2}H_2O$, $CaSO_4 \cdot H_2O$); dry alum; calcium oxide (CaO); magnesium oxide (MgO); carbonates such as potassium carbonate ($K_2CO_3$) and sodium carbonate ($Na_2CO_3$); bromides such as magnesium bromide ($MgBr_2$), calcium bromide ($CaBr_2$) and aluminum bromide ($AlBr_3$); iodides such as magnesium iodide ($MgI_2$, $MgI_2 \cdot 6H_2O$), calcium iodide ($CaI_2$) and aluminum iodide ($AlI_3$); zeolite; and sodium hydrogenphosphate ($Na_2HPO_4$). Some embodiments may include anhydrous inorganic salts such as calcium sulfate ($CaSO_4$), magnesium sulfate ($MgSO_4$), calcium chloride ($CaCl_2$)), magnesium chloride ($MgCl_2$), calcium oxide (CaO), and mixtures thereof, in view of their effective heat generation, mildness to hair and/or skin, and easy handling. Some embodiments may include anhydrous magnesium sulfate ($MgSO_4$).

The inorganic heat generating agents useful herein may have an average diameter of, preferably from about 0.01 µm to about 200 µm, more preferably from about 0.05 µm to about 30 µm, still more preferably from about 0.1 µm to about 20 µm, in view of preventing gritty feel.

The inorganic heat generating agent may be included in the compositions at a level by weight of the first composition of from about 5% to about 60%, in some embodiments from about 8% to about 50%, other embodiments from about 10% to about 35%, from about 10% to about 30%, from about 12% to about 20%.

Phase Changing Agents

The anhydrous cosmetic first compositions of the present invention may comprise a phase changing agent dispersed in an inert carrier. It is believed that the phase changing agent, having a certain melting point of the present invention, can absorb heat from the heat generating agent by changing its phase from solid to liquid, and then release the heat slowly by changing its phase from liquid to solid. Thus, it is believed that the phase changing agent can prevent the compositions from warming up to a higher temperature than expected and provide prolonged warming from the compositions, without using coated heat generating agents.

The phase-changing agents of the present invention may have a melting point of from about 30° C. to about 70° C., preferably from about 30° C. to about 60° C., more preferably from about 35° C. to about 50° C. This melting point can be that of one kind of material. The melting point can also be a mixture of 2 or more kinds of materials, when 2 or more materials are miscible with each other. In this case, each material does not necessarily have a melting point of from about 30° C. to about 70° C., however, mixtures thereof have a melting point of from about 30° C. to about 70° C.

The phase-changing agents useful herein include, for example, amidoamines; fatty compounds such as fatty alcohols, fatty acids, fatty alcohol derivatives, fatty acid derivatives, and mixtures thereof; hydrocarbons such as solid paraffin; and mixtures thereof. Fatty compound useful herein are disclosed below under the title "High Melting Point Fatty Compound". Amidoamines useful herein are disclosed below under the title "Amidoamine". Preferred phase changing agents are fatty compounds such as fatty alcohols, fatty acids, fatty alcohol derivatives, fatty acid derivatives, and mixtures thereof; amidoamines, and mixtures thereof, in view of providing conditioning benefit. More preferred are fatty alcohols selected from the group consisting of cetyl alcohol (melting point=46-55° C.), stearyl alcohol (melting point=54-61° C.), and mixtures thereof, still more preferred are mixtures of cetyl alcohol and stearyl alcohol having a weight ratio of cetyl alcohol to stearyl alcohol of from about 10:90 to about 99:1 (melting point from about 48° C. to about 58° C.). In order to function as a phase changing agent, materials are dispersed, but not dissolved in an inert carrier. Materials completely dissolved in an inert carrier, even if they have a melting point of from about 30° C. to about 70° C., cannot function as the phase changing agents of the present invention. For example, Japanese Patent Laid-open No. H11-228332 discloses a composition containing 5 wt % of myristyl myristate having a melting point of from 41 to 43° C. and 65 wt % of octyl stearate carrier (in Example 9), however, 5 wt % of myristyl myristate is completely dissolved in 65 wt % of octyl stearate carrier, thus, it cannot function as the phase changing agent of the present invention.

In the present invention, in order to make phase changing agents dispersed in an inert carrier, materials which are insoluble in the inert carrier are used, or materials are contained at a higher level than its saturation point in the inert carrier. Materials having a lower solubility to an inert carrier are preferably used. The solubility depends on each combination of phase changing agents and inert carriers. For example, preferable combinations of phase changing agents and inert carriers include; the combination of high melting point fatty compound as phase changing agent, and polyethylene glycol as an inert carrier; the combination of high melting point fatty compound as phase changing agent, and glycerin as an inert carrier; the combination of high melting point fatty compound as phase changing agent, and low melting point ester oils as an inert carrier; the combination of high melting point fatty compound as phase changing agent, and liquid paraffin as an inert carrier; the combination of hydrocarbons such as solid paraffin as phase changing agent, and polyethylene glycol as an inert carrier. More preferred are; the combination of fatty alcohols selected from the group consisting of cetyl alcohol, stearyl alcohol, and mixtures thereof as phase changing agents, and polyethylene glycol as an inert carrier; the combination of fatty alcohols selected from the group consisting of cetyl alcohol, stearyl alcohol, and mixtures thereof as phase changing agents, and glycerin as an inert carrier; the combination of fatty alcohols selected from the group consisting of cetyl alcohol, stearyl alcohol, and mixtures thereof as phase changing agents, and pentaerythritol ester oils as an inert carrier. The phase changing agent can be included in the compositions at a level by weight of, preferably from about 0.2% to about 20%, more preferably from about 0.5% to about 15% still more preferably from about 1% to about 10%.

Polyoxyalkylene Derivatives

The anhydrous first composition of the present invention may comprise polyoxyalkylene derivatives. It is believed that polyoxyalkylene derivatives can help the dispersion of inorganic heat generating agents in inert carriers, thus, prevent the agglomeration of inorganic heat generating agents which causes a gritty feel to the skin and/or hair. It is also believed that some of the polyoxyalkylene derivatives can provide a slippery feel, which eases the gritty feel caused by the inorganic heat generating agents.

The polyoxyalkylene derivatives useful herein are preferably water soluble polyoxyalkylene derivatives. The polyoxyalkylene derivatives useful herein may include, for example, polyoxyethylene/polyoxypropylene copolymer, polyoxyethylene alkyl ether, polyoxypropylene alkyl ether, polyoxyethylene alkyl ether ester, polyoxypropylene alkyl ether ester, polyoxyethylene glyceryl ester, polyoxypropylene glyceryl ester, and mixtures thereof. Among them, polyoxyethylene/polyoxypropylene copolymers may preferably be used in view of preventing agglomeration of inorganic heat generating agents, and polyoxyethylene glyceryl esters may preferably be used in view of providing slippery feel.

When the polyoxyalkylene derivative is used in view of preventing agglomeration of inorganic heat generating agents, the polyoxyalkylene derivative may be included in the compositions at a level by weight of, preferably from about 0.1% to about 10%, more preferably from about 0.5% to about 10%, still more preferably from about 1% to about 5%. When the polyalkylene derivative is used in view of providing slippery feel, the polyoxyalkylene derivative may be included in the compositions at a level by weight of, preferably from about 10% to about 90%, more preferably from about 15% to about 85%, still more preferably from about 20% to about 80%.

Preferred polyoxyethylene alkyl ethers are, for example, those of the formula $RO(CH_2CH_2O)_nH$, wherein n is from 1 to about 200, preferably from about 20 to about 100, and R is an alkyl having from about 8 to about 22 carbon atoms.

Preferred polyoxyethylene glyceryl esters include, for example, following (i) and (ii).

(i) PEG-Odified Glycerides having the Structure:

wherein one or more of the R groups is selected from saturated or unsaturated fatty acid moieties derived from animal or vegetable oils such as palmitic acid, lauric acid, oleic acid or linoleic acid wherein the fatty acid moieties have a carbon length chain of from 12 and 22, any other R groups are hydrogen, x, y, z are independently zero or more, the average sum of x+y+z (the degree of ethoxylation) is equal to from about 10 to about 45. Preferably, the PEG-modified glycerides have an HLB value of about 20 or less, more preferably about 15 or less, still preferably about 11 or less. Preferably, the PEG-modified glycerides have from 2 to 3 fatty acid R groups, more preferred have 3 fatty acid R groups (PEG-modified triglycerides). Preferably, the average sum of x+y+z (the degree of ethoxylation) is equal to from about 20 to 30, more preferred is an average sum of 5. Most preferred are PEG-substituted triglycerides having 3 oleic acid R groups, wherein the average degree of ethoxylation is about 25 (PEG-25 glyceryl trioleate). Preferred commercially available PEG-modified triglycerides include Tagat TOO, Tegosoft GC, Tagat BL 276®, (all three manufactured by Evonik Industries AG) and Crovol A-40, Crovol M-40 (manufactured by Croda Corporation). Other preferred commercially available PEG-modified triglycerides include Tagat S® and Tagat S 2® (manufactured by Evonik Industries AG).

(ii) PEG-Modified Glyceryl Fatty Acid Esters having the Structure:

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms. Suitable polyethylene glycol derivatives of glycerides can be polyethylene glycol derivatives of hydrogenated castor oil. For example, PEG-20 hydrogenated castor oil, PEG-30 hydrogenated castor oil. PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil. Preferred for use in the compositions herein is PEG-60 hydrogenated castor oil. Other suitable polyethylene glycol derivatives of glycerides can be polyethylene glycol derivatives of stearic acid, for example, PEG-30 stearate, PEG-40 stearate, PEG-50 stearate, PEG-75 stearate, PEG-90 stearate, PEG-100 stearate, PEG-120 stearate, and PEG-150 stearate. Preferred for use in the compositions herein is PEG-100 stearate.

Preferred polyoxyethylene/polyoxypropylene copolymers include, for example, polyoxyethylene/polyoxypropylene random copolymer and polyoxyethylene/polyoxypropylene block copolymer. Among these polyoxyalkylene derivatives, polyoxyethylene/polyoxypropylene copolymers including polyoxyethylene/polyoxypropylene random copolymer and polyoxyethylene/polyoxypropylene block copolymer are preferably used in the composition of the present invention in view of their suspending benefit. More preferred is polyoxyethylene/polyoxypropylene block copolymer, still more preferred is polyoxyethylene/polyoxypropylene block copolymer having a weight ratio of polyoxyethylene to polyoxypropylene of from about 5:10 to about 8:10, even more preferred is the block copolymer having the ratio of 8:10.

Commercially available polyoxyalkylene derivatives useful herein include: polyoxyethylene/polyoxypropylene block copolymer; having CTFA name Poloxamer 338, available from BASF under trade name Pluronic F-108, and also available from Sanyo Chemical under trade name Newpol PE-108; and having CTFA name Poloxamer 288, available from BASF under trade name Pluronic F-98, and also available from Sanyo Chemical under trade name Newpol PE-98.

Inert Carrier

The anhydrous first composition of the present invention preferably comprises an inert carrier. The inert carrier is included in the first composition at a level by weight of from about 3% to about 90%, in some embodiments from about 25% to about 90%, in still other embodiments from about 30% to about 85%, and in some embodiments from about 10% to about 70%, by weight of the first composition.

The inert carriers useful herein are liquid carriers and include; for example, liquid polyhydric alcohols such as polyethylene glycol, polypropylene glycol, 1,2-propane diol or propylene glycol, 1,3-propane diol, hexylene glycol, glycerin, diethylene glycol, dipropylene glycol, 1,2-butylene glycol, 1,4-butylene glycol, ethanol, sorbitol, diglycerin, polyglycerols; liquid paraffin; mineral oil; vegetable oil; low melting point oil such as pentaerythritol tetraisostearate; and mixtures thereof. The liquid polyhydric alcohols such as polyethylene glycol can also be used as additional heat generating agents. Preferred are polyethylene glycol, polypropylene glycol, glycerin, diglycerin, sorbitol, liquid paraffin, mineral oil, vegetable oil, pentaerythritol tetraisostearate, and mixtures thereof in view of physical properties such as viscosity and fluidity. More preferred is polyethylene glycol in view of its ability to generate a heat by mixing with water and physical properties such as viscosity and fluidity.

The polyethylene glycols useful herein are those having the formula:

wherein n has an average value of from 4 to 12.

The polyethylene glycol described above is also known as a polyethylene oxide, and polyoxyethylene. Polyethylene glycols useful herein that are especially preferred are PEG-200 wherein n has an average value of about 4. Commercially available preferred polyethylene glycol includes, for example, PEG-4 having trade name Pluracare E 200 available from BASF.

Reaction Control Agents

The anhydrous first compositions of the present invention preferably contain reaction control agents which can control the heat generating reaction of the inorganic heat generating agent. The reaction control agents may slow down the reaction or accelerate the reaction. The reaction control agents may also control the temperature to which the first composition warms up.

Acids can be used as reaction control agents for accelerating the reaction of the inorganic heat generating agents. The acid useful herein includes, for example, citric acid, sodium diphosphate, potassium diphosphate, 1-glutamic acid, lactic acid, hydrochloric acid, malic acid, succinic acid, acetic acid, fumaric acid, 1-glutamic acid hydrochloride, tartaric acid, and mixtures thereof; preferably 1-glutamic acid, lactic acid, hydrochloric acid, and mixtures thereof. Among the above acids, citric acid is preferably used herein. Some acids can also be used together with amidoamines for providing conditioning benefits as described below. The acid can be contained at a level such that the mole ratio of the inorganic heat generating agent to acid is from about 1:0.1 to about 1:10, preferably from about 1:0.5 to about 1:5. Water absorbing polymer can be used as reaction control agents for slowing down the reaction of the inorganic heat generating agent. The water absorbing polymer useful herein includes, for example, vinyl polymers such as cross-linked acrylic acid polymers with the CTFA name Carbomer, carboxylic acid/carboxylate copolymers such as acrylic acid/alkyl acrylate copolymers with the CTFA name Acrylates/C10-30 Alkyl Acrylate Crosspolymer, cellulose derivatives and modified cellulose polymers such as hydroxyethylcellulose and hydroxypropyl cellulose, polyvinylpyrrolidone, polyvinyl alcohol, guar gum, other gums, starch-based polymers, alginic acid-based polymers, acrylate polymers, polyalkylene glycols having a molecular weight of more than about 1000, and mixtures thereof. These water absorbing polymers can also be used as viscosity modifying agents, described below.

Among the above water absorbing polymers, preferred are cellulose derivatives and modified cellulose polymers, and more preferred is Hydroxyethylcellulose. The water absorbing polymers can be included in the first composition, at a level by weight of, preferably from about 0.2% to about 20%, more preferably from about 0.5% to about 15%, still more preferably from about 1% to about 10%.

Heat Reserving Materials

The anhydrous first compositions of the present invention may contain heat reserving materials which can reserve a heat. The heat reserving material can be used for prolonging heating, and may be used for slowing down the warming speed, and may also control the temperature to which the cosmetic composition warms up.

The heat reserving materials include, for example, silica gel, carboxymethyl cellulose gel, phase-changing materials, and mixtures thereof. The phase-changing materials useful herein are those which have a melting point of from about 25° C. to about 80° C. The phase-changing materials useful herein include, for example, a fatty compound such as fatty alcohol and fatty acid; hydrocarbons; a mixture of hydrocarbons and foamed polyolefin; and mixtures thereof. Fatty compound useful herein are disclosed below as high melting point fatty compounds.

The heat reserving material can be included in the first compositions at a level by weight of, preferably from about 0.2% to about 20%, more preferably from about 0.5% to about 15% still more preferably from about 1% to about 10%.

Viscosity Modifying Agent

The anhydrous first composition of the present invention may contain a viscosity modifying agent. The viscosity modifying agent useful herein includes, for example, vinyl polymers such as cross linked acrylic acid polymers with the CTFA name Carbomer, carboxylic acid/carboxylate copolymers such as acrylic acid/alkyl acrylate copolymers with the CTFA name Acrylates/C10-30 Alkyl Acrylate Crosspolymer, cellulose derivatives and modified cellulose polymers, polyvinylpyrrolidone, polyvinyl alcohol, guar gum, other gums, starch-based polymers, alginic acid-based polymers, acrylate polymers, polyalkylene glycols having a molecular weight of more than about 1000, inorganic water soluble material such as bentonite, aluminum magnesium silicate, laponite, hectorite, and anhydrous silicic acid, and mixtures thereof. The polymers described herein can also be used as the viscosity modifying agent. Some polyalkylene glycols described herein can also be used as hair conditioning agents.

The viscosity modifying agent can be included in the compositions at a level by weight of, preferably from about 0.01% to about 5%, more preferably from about 0.05% to about 3% still more preferably from about 0.1% to about 3%.

Additional Heat Generating Agents

The anhydrous first compositions of the present invention may contain additional heat generating agents, in addition to the inorganic heat generating agents, which generate a heat by mixing with water. Such additional heat generating agents useful herein include, for example, organic heat generating agents such as polyhydric alcohols.

The polyhydric alcohol useful herein includes, for example, polyethylene glycol, polypropylene glycol, 1,2-propane diol or propylene glycol, 1,3-propane diol, hexylene glycol, glycerin, diethylene glycol, dipropylene glycol, 1,2-butylene glycol, 1,4-butylene glycol, ethanol, 1-propanol, 1-butanol, 2-propanol, erythritol, threitol, xylitol, sorbitol, mannitol, galactitol, iditol, inositol, diglycerin, polyglycerols, polyglycerol fatty acid esters, and mixtures thereof. These can also be used as the inert carrier described above.

Such additional heat generating agents can be included in the first compositions at a level by weight of, preferably from about 2% to about 85%, more preferably from about 5% to about 85%, still more preferably from about 10% to about 85%.

Hair Conditioning Composition

The anhydrous cosmetic compositions of the present invention are preferably anhydrous hair care compositions, more preferably anhydrous hair conditioning compositions. The anhydrous hair conditioning compositions preferably comprise hair conditioning agents in addition to the above described heat generating agent, the phase changing agent, and the inert carrier. The hair conditioning agents useful herein include, for example, high melting point fatty compounds, amidoamines, acids, cationic conditioning agents such as cationic surfactants and cationic polymers, low melting point oils, silicone compounds, polypropylene glycol, polyethylene glycol, and mixtures thereof. Among these hair conditioning agents, preferred are high melting point fatty compounds, amidoamines, acids and mixtures thereof.

High Melting Point Fatty Compound

The hair conditioning composition of the present invention preferably comprises a high melting point fatty compound. The high melting point fatty compound can be used as the "Phase Changing Agent" described above.

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The high melting point fatty compound can be included in the composition at a level by weight of, preferably from about 0.1% to about 30%, more preferably from about 0.2% to about 0.25%, still more preferably from about 0.5% to about 15%.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present: ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Commercially available high melting point fatty compounds useful herein include: cetyl alcohol, stearyl alcohol, and behenyl alcohol having tradenames CONOL series available from Shin Nihon Rika (Osaka, Japan), and NAA series available from NOF (Tokyo, Japan).

Amidoamine

The hair conditioning composition of the present invention preferably comprises an amidoamine of the following general formula:

wherein $R^1$ is a residue of $C_{11}$ to $C_{24}$ fatty acids. $R^2$ is a $C_1$ to $C_4$ alkyl, and m is an integer from 1 to 4.

The amidoamine can be included in the composition at a level by weight of, preferably from about 0.05% to about 10%, more preferably from about 0.05% to about 8%, still more preferably from about 0.1% to about 5%.

Preferred amidoamines useful in the present invention includes stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylarmne, behenamidopropyldimethylanine, behenamidopropyldiethylamine, behenamidoethyldiethylamine, behenamidoethyldimethylamine, arachidanidopropyldimethylamine, arachidamidopropyldiethylamine, arachidamidoethyldiethylamine, arachidamidoethyldimethylamme, and mixtures thereof; more preferably stearamidopropyldimethylamine, stearamidoethyldiethylamine, and mixtures thereof. Commercially available amidoamines useful herein include: stearamidopropyldimethylanine having tradename SAPDMA available from Inolex, and tradename Amidoamine MPS available from Nikko.

Acids

The hair conditioning composition of the present invention preferably comprises an acid selected from the group consisting of L-glutamic acid, lactic acid, hydrochloric acid, malic acid, succinic acid, acetic acid, fumaric acid, L-glutamic acid hydrochloride, tartaric acid, and mixtures thereof;

preferably L-glutamic acid, lactic acid, hydrochloric acid, and mixtures thereof. The acid described herein can also be used as the "Reaction Control Agent" described above. The acid can be contained at a level such that the mole ratio of amidoamine to acid is, preferably from about 1:0.3 to about 1:1, more preferably from about 1:0.5 to about 1:0.9 Commercially available acids useful herein include: L-Glutamic acid; L-Glutamic acid (cosmetic grade) available from Ajinomoto.

Cationic Conditioning Agent

The hair conditioning composition of the present invention may contain a cationic conditioning agent.

The cationic conditioning agent can be included in the composition at a level by weight of, preferably from about 0.1% to about 10%, more preferably from about 0.25% to about 8%, still more preferably from about 0.5% to about 3%.

The cationic conditioning agent is selected from the group consisting of cationic surfactants, cationic polymers, and mixtures thereof.

Cationic Surfactant

The cationic surfactant useful herein is any known to the artisan and described below.

Among the cationic surfactants useful herein are those corresponding to the general formula (I):

(I)

wherein at least one of $R^1$, $R^2$, $R^3$, and $R^4$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^1$, $R^2$, $R^3$, and $R^4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups. e.g., those of about 12 carbons, or higher, can be saturated or unsaturated. Preferred is when $R^1$, $R^2$, $R^3$, and $R^4$ are independently selected from Ci to about $C_{22}$ alkyl. Nonlimiting examples of cationic surfactants useful in the present invention include the materials having the following CTFA designations, quaternium-8, quaternium-14, quaternium-18, quaternium-18 methosulfate, quaternium-24, and mixtures thereof.

Among the cationic surfactants of general formula (I), preferred are those containing in the molecule at least one alkyl chain having at least 16 carbons. Nonlimiting examples of such preferred cationic surfactants include: behenyl trimethyl ammonium chloride available, for example, with tradename INCROQUAT TMC-80 from Croda and ECONOL TM22 from Sanyo Kasei; cetyl trimethyl ammonium chloride available, for example, with tradename CA-2350 from Nikko Chemicals, hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^1$-$R^4$ radicals contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Preferred hydrophilically substituted cationic surfactants include those of the formula (II) through (VIII) below:

(II)

wherein n is from 8 to about 28, x+y is from 2 to about 40, $Z^1$ is a short chain alkyl, preferably a $C_1$-$C_3$ alkyl, more preferably methyl, or $(CH_2CH_2O)zH$ wherein x+y+z is up to 60, and X is a salt forming anion as defined above;

(III)

wherein m is 1 to 5, one or more of $R^5$, $R^6$, and $R^7$ are independently an $C_1$-$C_{30}$ alkyl, the remainder are $CH_2CH_2OH$, one or two of $R^8$, $R^9$, and $R^{10}$ are independently an $C_1$-$C_{30}$ alkyl, and remainder are $CH_2CH_2OH$, and X is a salt forming anion as mentioned above;

(IV)

-continued (V)

wherein, independently for formulae (IV) and (V). $Z^2$ is an alkyl, preferably a $C_1$-$C_3$ alkyl, more preferably methyl, and $Z^3$ is a short chain hydroxyalkyl, preferably hydroxymethyl or hydroxyethyl, p and q independently are integers from 2 to 4, inclusive, preferably from 2 to 3, inclusive, more preferably 2. $R^{11}$ and $R^{12}$, independently, are substituted or unsubstituted hydrocarbyls, preferably $C_{12}$-$C_{20}$ alkyl or alkenyl, and X is a salt forming anion as defined above;

(VI)

wherein $R^{13}$ is a hydrocarbyl, preferably a $C_1$-$C_3$ alkyl, more preferably methyl. $Z^4$ and $Z^5$ are, independently, short chain hydrocarbyls, preferably $C_2$-$C_4$ alkyl or alkenyl, more preferably ethyl, a is from 2 to about 40, preferably from about 7 to about 30, and X is a salt forming anion as defined above:

(VII)

wherein $R^{84}$ and $R^{85}$, independently, are $C_1$-$C_3$ alkyl, preferably methyl, $Z^6$ is a $C_{12}$-$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

(VIII)

wherein b is 2 or 3. $R^{16}$ and $R^{17}$, independently are $C_1$-$C_3$ hydrocarbyls preferably methyl, and X is a salt forming anion as defined above. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof, for example, commerically available under the following tradename; TETRANYL CO-40 from Kao Chemicals.

Second Composition

The second composition of the present invention may comprise an oil phase and an aqueous phase.

Details of Oil Phase Composition

The oil phase may comprise the surfactants and the high melting point fatty compounds. The oil phase comprises preferably from about 50% to about 100%, more preferably from about 60% to about 100%, still more preferably from about 70% to about 100% of the surfactants and the high melting point fatty compounds, by weight of the total amount of the surfactants and the high melting point fatty compounds used in the second composition.

The surfactants and the high melting point fatty compounds are present in the oil phase, with or without other ingredients, at a level by weight of the oil phase of, preferably from about 35% to about 100%, more preferably from about 50% to about 100%, still more preferably from about 60% to about 100%.

The oil phase may contain an aqueous carrier such as water, lower alkyl alcohols, and/or polyhydric alcohols. If included, the level of aqueous carrier in the oil phase is up to about 50%, more preferably up to about 40%, still more preferably up to about 25%, even more preferably up to about 15% by weight of the oil phase, in view of providing the benefits of the present invention. Among the aqueous carrier, it is further preferred to control the level of water in the oil phase, such that the level of water in the oil phase is preferably up to about 40%, more preferably up to about 25%, still more preferably up to about 15%, even more preferably up to about 10% by weight of the oil phase. The oil phase may be substantially free of water. In the present invention, "oil phase being substantially free of water" means that: the oil phase is free of water; the oil phase contains no water other than impurities of the ingredients; or, if the oil phase contains water, the level of such water is very low. In the present invention, a total level of such water in the oil phase, if included, preferably 1% or less, more preferably 0.5% or less, still more preferably 0.1% or less by weight of the oil phase.

The oil phase may contain other ingredients than the surfactants and the high melting point fatty compounds and aqueous carrier. Such other ingredients are, for example, water-insoluble components and/or heat sensitive components, such as water-insoluble silicones, water-insoluble perfumes, water-insoluble preservatives such as parabens and non-heat sensitive preservatives such as benzyl alcohol. In the present invention, "water-insoluble components" means that the components have a solubility in water at 25° C. of below 1 g/100 g water (excluding 1 g/100 water), preferably 0.7 g/100 g water or less, more preferably 0.5 g/100 g water or less, still more preferably 0.3 g/100 g water or less. If included, it is preferred that the level of such other ingredients in the oil phase is up to about 50%, more preferably up to about 40%, by weight of the oil phase, in view of providing the benefits of the present invention.

Details of Aqueous Phase Composition

The aqueous phase comprises an aqueous carrier. The aqueous phase comprises preferably from about 50% to about 100%, more preferably from about 70% to about 100%, still more preferably from about 90% to about 100%, even more preferably from about 95% to about 100% of aqueous carrier, by weight of the total amount of the aqueous carrier used in the second composition.

The aqueous carrier is present in the aqueous phase, with or without other ingredients, at a level by weight of the aqueous phase of, from about 50% to about 100%, more preferably from about 70% to about 100%, still more preferably from about 90% to about 100%, even more preferably from about 95% to about 100%.

The aqueous phase may contain the surfactants and high melting point fatty compounds. If included, it is preferred that the level of the sum of the surfactants and high melting point fatty compounds in the aqueous phase is up to about 20%, more preferably up to about 10%, still more preferably up to about 7% by weight of the aqueous phase, in view of providing the benefits of the present invention. Even more preferably, the aqueous phase is substantially free of the surfactants and high melting point fatty compounds. In the present invention, "aqueous phase being substantially free of the surfactants and high melting point fatty compounds" means that: the aqueous phase is free of the surfactants and high melting point fatty compounds; or, if the aqueous phase contains the surfactants and high melting point fatty compounds, the level of such surfactants and high melting point fatty compounds is very low. In the present invention, a total level of such surfactants and high melting point fatty compounds in the aqueous phase, if included, preferably 1% or less, more preferably 0.5% or less, still more preferably 0.1% or less by weight of the aqueous phase.

The aqueous phase may contain other ingredients than the surfactants and the high melting point fatty compounds and aqueous carrier. Such other ingredients are, for example, water soluble components and/or heat sensitive components, such as water soluble pH adjusters, water soluble polymers and water soluble preservatives such as phenoxyethanol, Kathon® and sodium benzoate. In the present invention, "water soluble components" means that the components have a solubility in water at 25° C. of at least 1 g/100 g water, preferably at least 1.2 g/100 g water, more preferably at least 1.5 g/100 g water, still more preferably at least 2.0 g/100 water. If included, it is preferred that the level of such other ingredients in the aqueous phase is up to about 20%, more preferably up to about 10% by weight of the aqueous phase, in view of providing the benefits of the present invention.

The second composition of the present invention may comprise a surfactant, high melting point fatty compound, and aqueous carrier. The surfactants, the high melting point fatty compounds, and the aqueous carrier are in the form of emulsion.

Cationic Surfactant System

The compositions of the present invention may comprise a cationic surfactant system. The cationic surfactant system can be included in the composition at a level from about 0.5%, preferably from about 1%, more preferably from about 1.5%, still more preferably from about 1.8%, still more preferably from about 2.0%, and about 8%, preferably to about 5%, more preferably to about 4% by weight of the second composition, in view of providing the benefits of the present invention.

Preferably, in the present invention, the surfactant is water-insoluble. In the present invention, "water-insoluble surfactants" means that the surfactants have a solubility in water at 25° C. of below 1 g/100 g water (excluding 1 g/100 water), preferably 0.7 g/100 g water or less, more preferably 0.5 g/100 g water or less, still more preferably 0.3 g/100 g water or less.

Cationic surfactant system useful herein comprises a mono-alkyl quaternized ammonium salt cationic surfactant and some embodiments may include a di-alkyl cationic surfactant. It is believed that such combination of a mono-alkyl quaternized ammonium salt cationic surfactant and a di-alkyl cationic surfactant provides feel of quick rinse and/or feel of easy to spread through hair, compared to single use of mono-alkyl cationic surfactants which have one long alkyl chain which has from 12 to 30 carbon atoms. In the cationic surfactant system it is preferred that the weight ratio of the mono-alkyl quaternized ammonium salt cationic surfactant to the di-alkyl cationic surfactant is from about 1:1 to about 10:1, more preferably from about 1.5:1 to about 7:1, still more preferably from about 2:1 to about 5:1, in view of stability in rheology and conditioning benefits.

Mono-Alkyl Quaternized Ammonium Salt Cationic Surfactant

The mono-alkyl quaternized ammonium salt cationic surfactants useful herein are those having one long alkyl chain of preferably from 12 to 30 carbon atoms, more preferably from 16 to 24 carbon atoms, still more preferably from 18 to 22 carbon atoms, in view of conditioning benefits. Such mono-alkyl quaternized ammonium salt cationic surfactants useful herein are, for example, those having the formula (I):

wherein one of $R^{71}$, $R^{72}$, $R^{73}$ and $R^{74}$ is selected from an aliphatic group of from 12 to 30 carbon atoms, more preferably from 16 to 24 carbon atoms, still more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 12 to 30 carbon atoms, more preferably from 16 to 24 carbon atoms, still more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Among them, more preferred cationic surfactants are those having a longer alkyl group, i.e., C18-22 alkyl group.

Such cationic surfactants include, for example, behenyl trimethyl ammonium chloride, methyl sulfate or ethyl sulfate, and stearyl trimethyl ammonium chloride, methyl sulfate or ethyl sulfate.

Di-Alkyl Cationic Surfactant

Di-alkyl cationic surfactants useful herein are those having two long alkyl chains of from 12 to 30 carbon atoms, more preferably from 16 to 24 carbon atoms, still more preferably from 18 to 22 carbon atoms, including, for example, di-long alkyl quaternized ammonium salts. Such di-alkyl quaternized ammonium salts useful herein are those having the formula (I):

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The high melting point fatty compound can be included in the second composition at a level of from about 0.5%, preferably from about 1.0%, more preferably form about 1.5%, still more preferably from about 2%, even more preferably from about 4%, and to about 15%, preferably to about 6% by weight of the second composition, in view of providing the benefits of the present invention.

The high melting point fatty compound useful herein have a melting point of 25° C. or higher, preferably 40° C. or higher, more preferably 45° C. or higher, still more preferably 50° C. or higher, in view of stability of the emulsion, especially the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols may be used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present invention, more preferred fatty alcohols are cetyl alcohol, stearyl alcohol and mixtures thereof.

Commercially available high melting point fatty compounds useful herein include: cetyl alcohol, stearyl alcohol, and behenyl alcohol having tradenames CONOL series available from Shin Nihon Rika (Osaka, Japan), and NAA series available from NOF (Tokyo, Japan).

Gel Matrix

Preferably, in the present invention, the emulsion of the second composition is in the form of a gel matrix. The gel matrix comprises the cationic surfactant system, the high melting point fatty compound, and an aqueous carrier. The gel matrix is suitable for providing various conditioning benefits, such as a slippery feel during the application to wet hair and softness and moisturized feel on dry hair.

Preferably, especially when the gel matrix is formed, the total amount of the cationic surfactant and the high melting point fatty compound is from about 1.0%, preferably from about 2.0%, more preferably from about 3.0% by weight of the composition, in view of providing the benefits of the present invention, and to about 15%, preferably to about 14%, more preferably to about 13%, still more preferably to about 10% by weight of the composition, in view of spreadability and product appearance. Furthermore, when the gel matrix is formed, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:4, still more preferably from about 1:2 to about 1:4, in view of providing improved wet conditioning benefits.

Preferably, when the gel matrix is formed, the composition of the present invention is substantially free of anionic surfactants and anionic polymers, in view of stability of the gel matrix. In the present invention, "the composition being substantially free of anionic surfactants and anionic polymers" means that the composition is free of anionic surfactants and anionic polymers; or, if the composition contains anionic surfactants and anionic polymers, the level of such anionic surfactants and anionic polymers is very low. In the present invention, a total level of such anionic surfactants and anionic polymers, if included, preferably 1% or less, more preferably 0.5% or less, still more preferably 0.1% or less by weight of the composition. Most preferably, the total level of such anionic surfactants and anionic polymers is 0% by weight of the composition.

Aqueous Carrier

The second composition of the present invention may comprise an aqueous carrier. The level and species of the carrier are selected according to the compatibility with other components and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the second compositions of the present invention comprise from about 20% to about 99%, preferably from about 30% to about 95%, and more preferably from about 80% to about 90% watery, by weight of the second composition.

Silicone Compound

The second composition may contain a silicone compound. It is believed that the silicone compound can provide smoothness and softness on dry hair. The silicone compounds herein can be used at levels by weight of the second composition of preferably from about 0.1% to about 20%, more preferably from about 0.5% to about 10%, still more preferably from about 1% to about 8%.

Preferably, the silicone compounds may have an average particle size of from about 1 microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$$A^-$; —N($R_2$)$CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Mother highly preferred amino silicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group.

The above aminosilicones, when incorporated into the second composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the second composition in the form of an emulsion, wherein the emulsion is made by mechanical mixing, or in the stage of synthesis through emulsion polymerization, with or without the aid of a surfactant selected from anionic surfactants, nonionic surfactants, cationic surfactants, and mixtures thereof.

Additional Components

The second composition of the present invention may include other additional components, which may be selected by the artisan according to the desired characteristics of the final product and which are suitable for rendering the second composition more cosmetically or aesthetically acceptable or to provide it with additional usage benefits. Such other additional components generally are used individually at levels of from about 0.001% to about 10%, preferably up to about 5% by weight of the composition.

A wide variety of other additional components can be formulated into the present compositions. These include other conditioning agents such as: hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; and sequestering agents, such as disodium ethylenediamine tetra-acetate; ultraviolet and infrared screening and absorbing agents such as benzophenones; and antidandruff agents such as zinc pyrithione and piroctone olamine.

Method of Manufacturing

The present invention is directed to a method of preparing a personal care composition, wherein the first composition can be prepared as described in US20030103930A1, and the second composition can be prepared as described in U.S. application Ser. No. 13/617,240.

The cosmetic composition of the present invention is a multi-phase composition in that it comprises first and second compositions that are kept separate from one another until dispensed. Although kept separate until dispensing, the first and second composition are put into contact upon dispensing. The warming benefit may not occur until the cosmetic composition is dispensed and the first and second compositions interact. A variety of approaches may be used to dispense a multi-phase product. A common method is a multi-chamber tube or bottle. As used herein "The first and second compositions are kept separated from one another" means, for example, a package comprising two chambers, wherein the first composition is contained in a first chamber and the second composition is contained in a separate second chamber. Such packages can be shaped as, for example, but not limited to, a tube, pump, bottle or upside-down bottle, sachet, or a blister pack.

In the present invention, the first composition and the second composition are not mixed before use. It is preferred that the first composition and the second composition are mixed at a ratio of from about 35:65 to about 98:2, more preferably to about 90:10, still more preferably from about 40:60 to about 60:40.

While warming conditioners are known, current anhydrous warming conditioners are not necessarily able to deliver top conditioning benefits, such as superior silicone delivery through the use of gel networks or gel matrices. Similarly, some high performing conditioners lack the ability to offer a warming benefit without sacrificing their performance benefits. The present invention, therefore, is able to deliver high performance conditioning benefits while also providing a warming benefit. The present inventors have discovered certain ratios and viscosities of the first and second compositions described herein may provide a synergistic warming benefit compared to existing warming conditioners, while still providing excellent silicone deposition.

Warming conditioners using an anhydrous inorganic salt are not activated until mixed with water. Typically, conditioners using such warming agents rely on the water of the shower, for example, to provide the water necessary to start the warming. The present inventions have discovered several things. First, an advantage may be had if the warming agent activation, that is, the triggering of heat that begins with the warming agent mixing with water, can happen in the user's hand, even before application on the hair and scalp. This allows for a superior warming benefit, as discussed below. But in order for the activation to occur in the hand, the water for activation must be provided in a form that is not as thin and runny as just water. That is, the warming agent must be mixed with a viscous-enough yet aqueous composition, such as the second composition of the present invention. In addition, this more robust mixture is more easily transferred from the hand to the hair, allowing the heat to be felt sufficiently on the head, that is, not one that is quickly and easily washed away.

The warming benefit of the present composition is superior to that of either the first composition or the second composition alone. Even though the first composition comprises a warming agent, use of the first composition alone, while also not providing superior silicone deposition, also is not able to deliver the warming benefit of the present invention's multi-phase composition.

Figure 1:
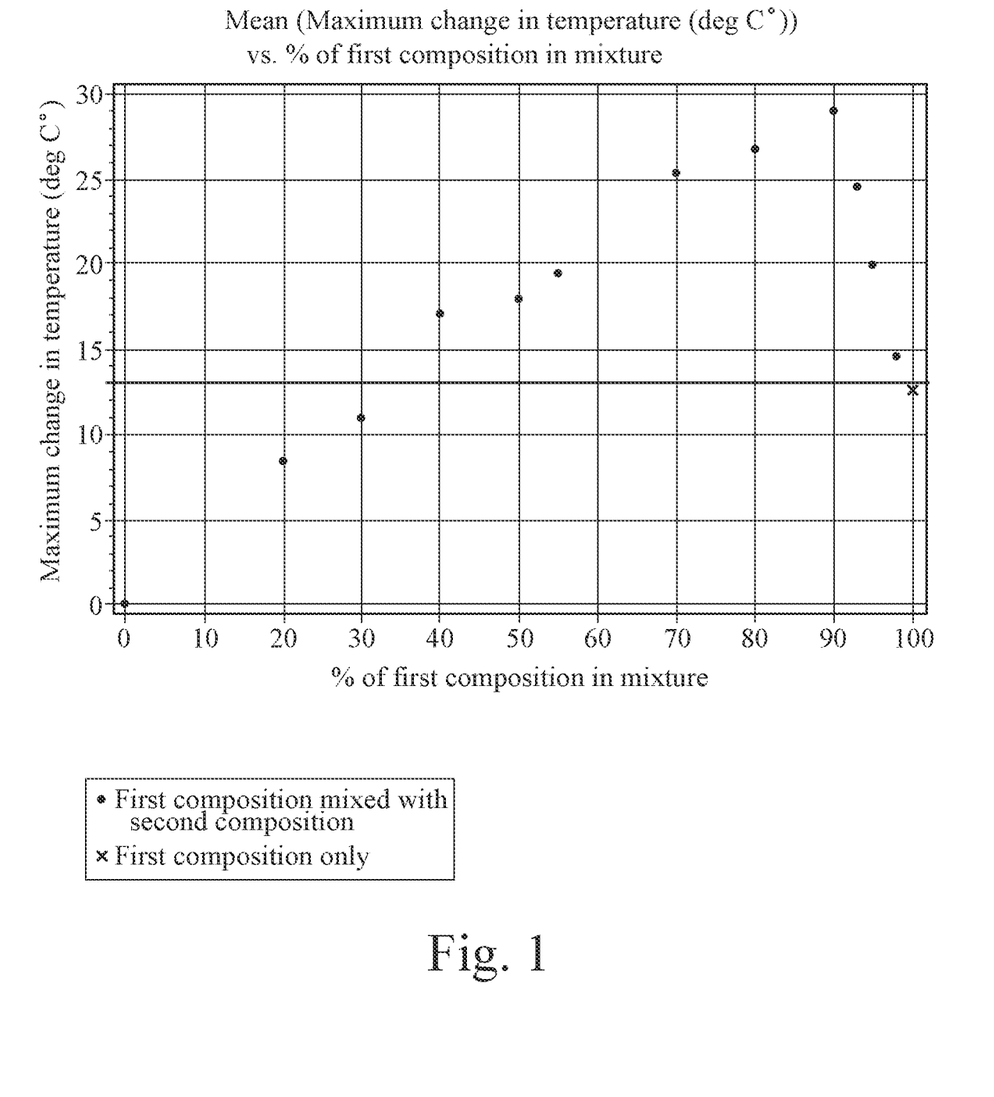
FIG. 1 is a graph of the maximum change of temperature for various hair conditioners.

For example, FIG. 1 is a graph of the maximum change in temperature a hair conditioner produces under the Maximum Temperature Change Test Method detailed below. The graph shows the maximum temperature change of various conditioners that are mixtures of the first and second compositions, specifically the compositions in Table 2. Table 1 is the data for FIGS. 1 and 2. The FIG. 1 graph also shows, with the x mark on the far right, the maximum temperature change for a hair conditioner that is 100% of the first composition in Table 2, which is the composition that comprises an inorganic heat generating agent, in this case 15% anhydrous magnesium sulfate. Surprisingly, the conditioner that is 100% first composition does not provide the highest maximum temperature change. When both compositions are mixed, the total percentages of warming agent (magnesium sulfate) are reduced. Yet, with the reduced amount of warming agent, the inventive formulas have a greater maximum temperature change.

The conditioner that is 100% first composition provides about 13 (12.63) degrees Celsius maximum temperature change or more, while the conditioner mixes that are 40%, 50%, 55%, 70%, 80%, 90%, 93%, 95%, and 98% of the first composition provide, respectively, 17.1, 17.4, 19.5, 25.4, 29.6, 29.1, 24.6, 20 and 14.6 degrees Celsius of maximum temperature change. As the FIG. 1 graph shows, even as the percentage of the first composition example I comprising an inorganic heat generating agent is reduced, some combinations with the second composition, which does not comprise any heat generating agent, produce a higher maximum temperature change than the first composition alone. That is, even though the weight percentage of heat generating agent in the overall mixture is lower, a greater warming benefit results. When the level of inorganic heat generating agent is increased in the first composition, more warming occurs and the maximum temperature change will subsequently increase.

One would expect that using a lower amount of magnesium sulfate would at least reduce the warming effect. However, the warming benefit of the present invention's multi-phase compositions is maintained and even is higher. The present inventors believe that the water in the second composition, delivered with a certain viscosity and in a certain ratio range with the first composition, allows for a synergistic boost to the magnesium sulfate's exothermic reaction.

Upon realizing this synergistic effect, the present inventors have isolated the particular ranges in which this effect exists. It is not simply a matter of combining a composition comprising a warming agent with some other aqueous composition, but becomes a matter of balancing the ratios of the first and second compositions, along with their respective viscosities in order to achieve the quick if not immediate mixing that allows the synergistic warming benefit to occur. Viscosity is a measure of how fluid the compositions are and thus how easily the compositions can be mixed together. Viscosities at a shear rate of 100 s$^{-1}$ are selected, as this low shear rate simulates the slow mixing of compositions on the palm by a consumer. As shown by the data, formulations that are outside certain ratios and viscosities do not produce the synergistic warming benefit, while those within the ratios and viscosities described herein exhibit the unexpected warming benefit. In the present invention, the viscosities between the first composition and the second composition may have a difference preferably less than 3.5 Pa·s and more preferably less than 3.1 Pa·s. It is believed that there is an upper limit to the difference in viscosities to exhibit the unexpected warming benefit. Beyond this upper limit, the viscosity difference is so great that it causes inhomogeneous mixing and thus delayed, less, or no warming benefit at the specified ratios.

Figure 2:
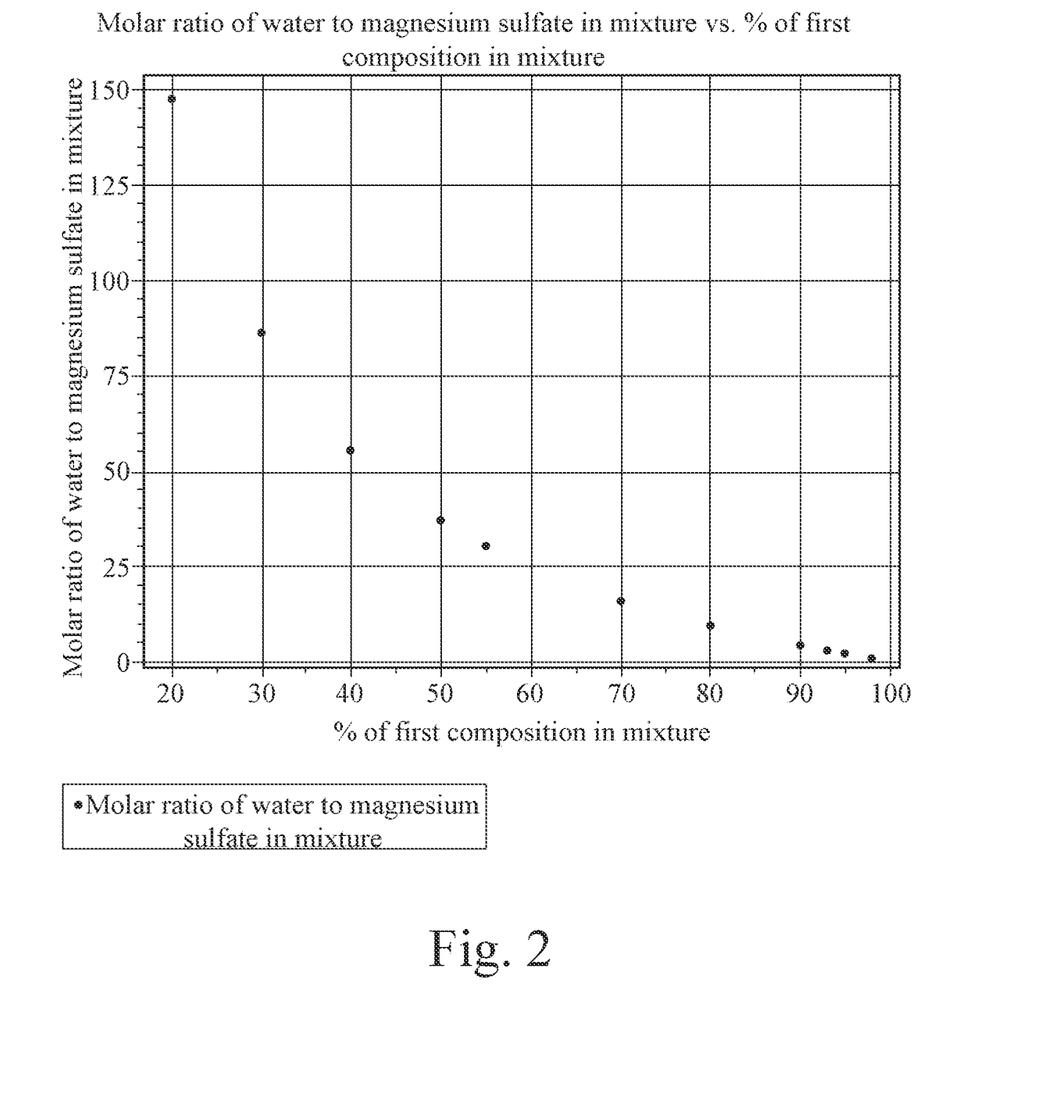
FIG. 2 is a graph of molar ratio of water to magnesium sulfate in the mixture versus the percent of the first composition in the mixture.

FIG. 2 is a graph that plots the molar ratio of water to magnesium sulfate in the mixture versus the percent of the first composition in the mixture. The graph shows that the molar ratio of water to magnesium sulfate that produces the synergistic warming benefit may be from about 75 to about 0.75. In some embodiments, the molar ratio of water in the second composition to the inorganic heating agent in the first composition may be from about 75 to about 0.75, which can then provide the unexpected warming benefit. If the molar ratio of water to inorganic heating agent is outside of this range, the warming benefit may not occur. The molar ratio that is effective can depend on the particular heating agent's enthalpy, wherein there may be an upper and lower limit to the molar ratio based on the heating agent's enthalpy.

TABLE 1

| % of first composition Ex I in mixture | % of second composition in mixture | Mean Maximum change in temperature (deg C.) | Total water content in both composition mixture (% w/w) | Total Magnesium sulfate in both composition mixture (% w/w) | Molar ratio of water to magnesium sulfate in mixture |
|---|---|---|---|---|---|
| 0 | 100 | 0 | 82.8 | 0.0 | 0 |
| 20 | 80 | 8.45 | 66.2 | 3.0 | 147.44 |
| 30 | 70 | 11.325 | 57.9 | 4.5 | 86.01 |
| 40 | 60 | 17.1 | 49.7 | 6.0 | 55.29 |
| 50 | 50 | 17.4 | 41.4 | 7.5 | 36.86 |
| 55 | 45 | 19.5 | 37.2 | 8.3 | 30.16 |
| 70 | 30 | 25.4 | 24.8 | 10.5 | 15.80 |
| 80 | 20 | 29.6 | 16.6 | 12.0 | 9.21 |
| 90 | 10 | 29.1 | 8.3 | 13.5 | 4.10 |
| 93 | 7 | 24.6 | 5.8 | 14.0 | 2.77 |
| 95 | 5 | 20 | 4.1 | 14.3 | 1.94 |
| 98 | 2 | 14.6 | 1.7 | 14.7 | 0.75 |
| 100 | 0 | 12.63 | 0.0 | 15.0 | 0 |

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

TABLE 2

Compositions (wt %)

| Components | First Composition Ex. I | First Composition Ex. II | Second Composition |
|---|---|---|---|
| BTMS/IPA *1 | — | — | 4.36 |
| BTAC/IPA *2 | 1.00 | 1.78 | — |
| CTAC/IPA *3 | 0.90 | — | — |
| Distearyl dimethyl ammonium Chloride | — | 0.8 | — |
| Cetyl alcohol | 1.00 | 0.5 | 1.73 |
| Stearyl alcohol | 1.80 | 1.3 | 4.32 |
| Benzyl alcohol | — | — | 0.40 |
| Disodium EDTA | — | — | 0.13 |
| Polysorbate 20 | — | — | 0.075 |
| Citric acid | — | — | 0.04 |
| Silicone compound | 4.20 (*4) | — | 5.00 (*5) |
| Polyethylene/polypropylene block copolymer *6 | 1.00 | 3.00 | — |
| Polypropylene glycol *7 | 19.33 | 19.33 | — |
| Methyl bis-(oleyl amidoethyl) 2-hydroxyethyl ammonium methosulfate *8 | 2.00 | 2.00 | — |
| Anhydrous magnesium sulfate | 15.00 | 20.00 | — |
| Preservatives | 0.3 | 0.3 | 0.03 |
| Perfume | 0.65 | — | 1.07 |
| Polyethylene glycol *9 | q.s. to 100% | q.s. to 100% | — |
| Deionized water | — | — | q.s. to 100% |
| Viscosity (Pa · s) | 1.88-3.60 | | 0.57-0.73 |
| Yield Stress (Pa) | 20.58-31.43 | | 1.12-3.05 |

Definitions of Components
*1 BTMS/IPA: 80% of Behenyl Trimethyl Ammonium Methosulfate and 20% of Isopropyl alcohol
*2 BTAC/IPA: 80% of Behentrimonium Chloride and 20% of Isopropyl Alcohol
*3 CTAC/IPA: 50% of Cetrimonium Chloride and 50% of Isopropyl Alcohol
*4 Silicone compound: Dimethicone having a viscosity of about 12,500 centistokes having a tradename Xiameter PMX-200 from Dow Corning.
*5 Silicone compound: Available from Momentive having a viscosity 10,000 mPa · s, and having following formula (I): $(R_1)_a G_{3-a}$—Si—$(-OSiG_2)_n$—$(-OSiG_b(R_1)_{2-b})_m$—O—$SiG_{3-a}(R_1)_a$ (I) wherein G is methyl; a is an integer of 1; b is 0, 1 or 2, preferably 1; n is a number from 400 to about 600; m is an integer of 0; $R_1$ is a monovalent radical conforming to the general formula $C_qH_{2q}L$, wherein q is an integer of 3 and L is —$NH_2$
*6 Polyethylene/polypropylene block copolymer: Available from Sanyo Chemical with tradename of Newpol-108.
*7 Polypropylene Glycol: Available from Sanyo Chemicals with tradename of Newpol PPG-34 L or Newpol PPG-2000
*8 Methyl bis-(oleyl amidoethyl) 2-hydroxyethyl ammonium methosulfate: Available from Kao Chemicals with tradename of Tetranyl CO-40
*9 Polyethylene glycol: Available from BASF with tradename Pluracare E200

Packaging

The package may comprise a first chamber and a second chamber, each chamber having an outlet thereto, wherein said anhydrous first composition is stored in said first chamber and said aqueous second composition is stored in said second chamber, said compositions being stored in isolation from each other and being arranged to be combined after passing through said respective outlets onto the skin. On combination of the compositions, heat is generated, effective to raise the temperature of the skin.

In expelling a portion of the contents of the package, each composition passes through the outlet of the chamber in which it is stored. The outlets may be adjacent so that on expelling the compositions from the package at the same time, they may be combined after they pass through the outlets onto the skin.

Although a heating effect is obtained as soon as the water comes into contact with the component that generates heat on contact with water, it is preferred to mix the compositions by rubbing them into the skin. In one embodiment, the package further comprises a dispensing nozzle through which the combined compositions are dispensed onto the skin. The aqueous and anhydrous compositions may be combined in the dispensing nozzle or a chamber leading thereto and then targeted onto the affected area of the skin.

In one embodiment, the package comprises a receptacle partitioned into first and second chambers. Preferably, the package comprises a lid that can be removed where each of first and second compositions can be removed from individual chambers through action of scooping using fingers. Yield stress of a product is the force that makes the product turn from solid-like to liquid-like. For easy scooping of product out of chambers using fingers while remaining solid-like on the Fingers without dripping off, the compositions need to have controlled yield stress. The compositions of the present invention have controlled yield stress for easy scooping of the first and second compositions out of chambers using fingers and without dripping off. It is preferred for the first composition to have a yield stress of preferably 1.0 Pa to 50 Pa and more preferably 15 Pa to 35 Pa. It is preferred for the second composition to have a yield stress of preferably 0.5 Pa to 5 Pa and more preferably 1.0 Pa to 3.5 Pa.

In another embodiment, the package comprises a tube comprising an anhydrous or aqueous composition and an inner tube comprising the other of said anhydrous or aqueous composition. Suitably, the inner tube is encompassed within an outer tube which forms the packaging. Preferably, the package is squeezable to expel said anhydrous or aqueous compositions. To consistently expel both first and second compositions from the said tube packaging when squeezed, the compositions' yield stresses are controlled. Product yield stress cannot be too high where a lot of force is required to turn the product from solid-like to liquid and to expel it from the tube. It is believed that there is a lower limit to the yield stress before the compositions naturally flows out of the tube by gravity when the tube cap is open. It is preferred for the first composition to have a yield stress of preferably 1.0 Pa to 50 Pa and more preferably 15 Pa to 35 Pa. It is preferred for the second composition to have a yield stress of preferably 0.5 Pa to 5 Pa and more preferably 1.0 Pa to 3.5 Pa.

Test Method

Maximum Temperature Change Test Method

Lab simulation of the warming sensation a consumer experiences on palm as the consumer spreads and mixes the product in shower. In a 20 ml plastic PE beaker, prepare a 10 g of the following: 1 g city water to simulate water on wet hands during shower, remaining 9 g of mixture of first and second composition depending on the ratios required. For example, when the ratio of the first composition to the second composition is 30:70, 2.7 g of the first composition and 6.3 g of the second composition are added to the 1 g city water. Thereafter, the mixture is stirred at one rotation per second with a digital thermometer with sensitivity of 1 decimal place. Temperature (° C.) is captured every second for the first minute and subsequently every 15 seconds up to total time of 1.5 minutes. For each composition ratio, the maximum temperature change from temperature at zero second is captured.

Product Yield Stress and Viscosity Test Method

The Yield stress and viscosity test method is used to determine the yield stress and viscosity of a gel-like/semi-solid product.

A controlled-stress rotational rheometer (such as Discovery HR-2, TA Instruments, New Castle, DE, USA, or equivalent) capable of sample temperature control (using a Peltier cooler and resistance heater combination) is used for the test.

The rheometer is operated in a parallel plate configuration with 40-mm 2° aluminum cone plate tooling. The rheometer is set at 25° C. Approximately 2 ml of sample is gently loaded onto peltier plate using a spatula from the sample jar without any shear to change the product structure, and excess protruding sample is trimmed once the gap reaches 50 μm after sample loading. Sample is then conditioned at 25° C. with 10 s$^{-1}$ shear rate for 60 seconds and equilibrated at 25° C. for 300 seconds before measurement starts. The test commences with rheometer generating a flow curve by increasing the strain rate from 0.1 s$^{-1}$ to 1000 s$^{-1}$ in logarithmic steps.

Analysis of the flow curve to obtain product yield stress is performed using the Python based library as described by Caggioni et al. 2020. Variations of the Hershel-Bulkley exponent reflecting contributions of the viscous continuous phase to the shear rate-dependent stress of soft glassy materials. Journal of Rheology 64, p 413.

Analysis of the flow curve to obtain product viscosity is performed by extracting the Viscosity (Pa·s) at shear rate of 100 s$^{-1}$ to simulate mixing of compositions on hand.

Method of Use

The composition of the present invention is preferably used for a method of conditioning hair, the method comprising following steps:
 (i) after shampooing hair, applying to the hair an effective amount of the conditioning composition for conditioning the hair; and
 (ii) then rinsing the hair.

Effective amount herein is, for example, from about 0.1 ml to about 2 ml per 10 g of hair, preferably from about 0.2 ml to about 1.5 ml per 10 g of hair.

The composition of the present invention provides improved conditioning benefits, especially improved wet conditioning benefits after rinsing and improved dry conditioning, while maintaining wet conditioning benefit before rinsing. The composition of the present invention may also provide improved product appearance to consumer. Thus, a reduced dosage of the composition of the present invention may provide the same level of conditioning benefits as those of a full dosage of conventional conditioner compositions. Such reduced dosage herein is, for example, from about 0.3 ml to about 0.7 ml per 10 g of hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair condition composition consisting of:
 (a) A first composition consisting of:
  Behentrimonium chloride
  Cetrimonium chloride
  Distearyl dimethyl ammonium chloride
  Cetyl alcohol
  Stearyl alcohol
  Dimethicone
  Polyethylene/polypropylene block copolymer
  Polypropylene glycol
  Methyl bis-(oleyl amidoethyl) 2-hydroxyethyl ammonium methosulfate
  Anhydrous Magnesium sulfate
  Preservatives
  Perfume
  Polyethylene glycol
 (b) A second composition consisting of:
  Behenyl trimethyl ammonium methosulfate
  Cetyl alcohol
  Stearyl alcohol
  Benzyl alcohol
  Disodium EDTA
  Polysorbate 20
  Citric acid
  Silicone compound
  Preservatives
  Perfume
  Deionized water wherein the difference in viscosities between the first and second composition is less than 3.5 Pa·s;

wherein the first and second compositions are kept separate from one another until dispensed; and wherein the hair conditioning composition when dispensed has a warming benefit.

2. The hair conditioning composition of claim 1, wherein the warming benefit of the hair conditioning composition is a maximum temperature change of greater than about 13 degree Celsius after the first composition and second composition are dispensed.

3. The hair conditioning composition of claim 1, wherein the hair conditioning composition is dispensed from a tube-in-tube package or a blister pack package; and the yield stress of the first composition is 15 Pa to 35 Pa and the yield stress of the second composition is 1.0 Pa to 3.5 Pa.

4. The hair conditioning composition of claim 1, wherein the weight ratio of the Behenyl trimethyl ammonium methosulfate and the mixture of cetyl alcohol and stearyl alcohol is from about 1:1 to about 1:4.

\* \* \* \* \*